(12) United States Patent
Kozawa et al.

(10) Patent No.: US 6,605,218 B2
(45) Date of Patent: Aug. 12, 2003

(54) DIALYZERS FOR BLOOD TREATMENT AND PROCESSES FOR PRODUCTION THEREOF

(75) Inventors: Hidetoshi Kozawa, Kyoto (JP); Hidekazu Nakashima, Shiga (JP); Shigehisa Wada, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/736,373

(22) Filed: Dec. 15, 2000

(65) Prior Publication Data

US 2001/0004976 A1 Jun. 28, 2001

(30) Foreign Application Priority Data

Dec. 21, 1999 (JP) .......................... 11-362960
Dec. 21, 1999 (JP) .......................... 11-362961
Dec. 21, 1999 (JP) .......................... 11-362962

(51) Int. Cl.$^7$ .......................... B01D 61/28; B01D 71/00; B01D 71/68
(52) U.S. Cl. .......................... 210/500.21; 210/500.1; 210/500.41
(58) Field of Search .......................... 210/500.1, 500.21, 210/500.41, 500.42, 500.24

(56) References Cited

U.S. PATENT DOCUMENTS

| | | | |
|---|---|---|---|
| 4,051,300 A | 9/1977 | Klein et al. .................... | 264/49 |
| 4,906,375 A | 3/1990 | Heilmann .............. | 210/500.23 |
| 5,436,068 A | 7/1995 | Kobayashi et al. .... | 210/500.41 |
| 5,762,798 A | 6/1998 | Wenthold et al. ...... | 210/500.23 |

OTHER PUBLICATIONS

Cabasso et al J. Applied Polymer Science vol. 20 2377–2394 (1976) Polysulfone Hollow Fibers I. Spinning and Properties.
Cabasso et al J. Applied Polymer Science vol. 21 165–180 (1977) Polysulfone Hollow Fibers II Morphology.
Cabasso et al J. Applied Polymer Science vol. 21 1883–1900 (1977) Porosity and Pore Size Determination in Polysulfone Hollow Fibers.
Cabasso Kirk–Othmer Encyclopedia of Chemical Technology vol. 12 3$^{rd}$ ed. 492–517 (1984) Hollow Fiber Membranes.

*Primary Examiner*—John Kim
(74) *Attorney, Agent, or Firm*—Nixon & Vanderhye P.C.

(57) ABSTRACT

A dialyzer for blood treatment includes a semipermeable membrane which is made of a hydrophobic polymer and a hydrophilic polymer, and has a water permeating performance drying of ½ or higher relative to that before drying. The dialyzer has a vitamin B12 clearance not smaller than 135 ml/min per 1.6 m$^2$ or the amount of the hydrophilic polymer eluted from the semipermeable membrane is not higher than 10 ppm. A dialyzer for blood treatment is light-weight, easy to handle, and exhibits a reduced elution of the hydrophilic polymer procedures for producing a dialyzer containing the semipermeable membrane and a process for producing a hollow fiber membrane for use in blood treatment as described.

4 Claims, No Drawings

DIALYZERS FOR BLOOD TREATMENT AND PROCESSES FOR PRODUCTION THEREOF

BACKGROUND OF THE INVENTION

1. Field of the Invention

The present invention relates to a semipermeable membrane for blood treatment which exhibits little change in performance upon drying and reduced elution of a hydrophilic polymer therefrom; a dialyzer for use in blood treatment using the same; and a processes for producing a dialyzer having incorporated therein a semipermeable membrane which exhibits little change in performance before and after drying and reduced elution of a hydrophilic polymer therefrom.

2. Description of the Related Art

As a material for a semipermeable membrane for blood treatment such as an artificial kidney, there have been used a number of materials. For example, a natural material cellulose and its derivatives, e.g., cellulose diacetate and cellulose triacetate, were originally used, and synthetic polymers were then developed, such as polysulfone, polymethyl methacrylate (PMMA) and polyacrylonitrile. Recently, modified cellulose membranes have also been used which is prepared by treating cellulose with polyethylene glycol (PEG) or the like to modify the compatibility to blood. In semipermeable membranes for blood treatment in patients suffering from chronic renal failure, attempts have been made to reduce the leakage of albumin to a minimum while positively removing low molecular proteins other than albumin. In addition to such improvement in the membranes, hemodiafiltration (HDF) procedures and push-and-pull procedures have been developed for increasing the dialysis efficiency and positive removal of undesirable low molecular proteins. Polysulfone, which has a high water permeability, is now widely used since it meets the above-mentioned requirements. In a polysulfone membrane, a hydrophilic polymer is generally blended to impart an affinity for blood to the membrane. However, the polysulfone membrane has such a defect that once it is dried the properties tend to be changed to a great extent. Hence, it is difficult to produce a dry type of polysulfone membrane dialyzer which is light-weight and easy to handle.

SUMMARY OF THE INVENTION

Accordingly, it is an object of the present invention to provide a dialyzer using a dry or semi-dry type of semipermeable membrane which has advantages such as light-weight and resistance to freeze, wherein the semipermeable membrane is improved in water permeability and dialyze performance (which are poor in a conventional one) to the same level as those of a wet type one.

It is another object of the present invention to provide a dry or semi-dry type of dialyzer having advantages such as light-weight and resistance to freeze, wherein the dialyzer is improved in water permeability and dialyze performance (which are poor in a conventional one) to the same level as those of a wet-type one and exhibits a reduced elution of a hydrophilic polymer therefrom.

That is, in an aspect of the present invention, there is provided a dialyzer for blood treatment having incorporated therein a semipermeable membrane which comprises a hydrophobic polymer and a hydrophilic polymer, the water permeating performance of the semipermeable membrane after drying being ½ or higher relative to that before drying and the dialyzer satisfying any of the following requirements:

(A) the vitamin B12 clearance is not smaller than 135 ml/min per 1.6 m²; and (B) the amount of the hydrophilic polymer that is eluted from the semipermeable membrane is not higher than 10 ppm.

In another aspect of the present invention, there is provided a process for producing a dialyzer having incorporated therein a semipermeable membrane which comprises a hydrophobic polymer and a hydrophilic polymer, the process comprising:

drying the semipermeable membrane; and saturating the dried semipermeable membrane with water ratio of not smaller than 100% based on the dry weight of the semipermeable membrane, providing an inert gas atmosphere to the inside of the dialyzer, and then irradiating the semipermeable membrane with gamma-ray in the inert gas atmosphere.

In still another aspect of the present invention, there is provided a process for producing a hollow fiber membrane for use in blood treatment through dry/wet spinning from a spinning solution comprising 15 to 18% by weight of a hydrophobic polymer and 4 to 8% by weight of a hydrophilic polymer, the dry zone being filled with dry mist.

DESCRIPTION OF THE PREFERRED EMBODIMENTS

In the present invention, the hydrophobic polymer to be used in the semipermeable membrane includes a number of engineering plastics, such as polysulfone, polyamide, polyimide, polyphenyl ether and polyphenylene sulfide. Preferably, the hydrophobic polymer is polysulfone represented by the formula below, which shows the skeleton of the polysulfone. Polysulfone derivatives in which the benzene ring in the skeleton is modified are also usable in the present invention.

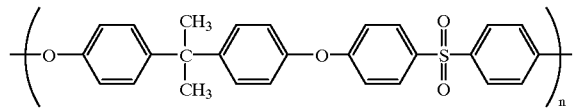

The hydrophilic polymer to be used in the semipermeable membrane includes, for example, polyethylene glycol, polyvinyl alcohol, carboxymethyl cellulose and polyvinyl pyrrolidone, which may be used alone or in combination. Polyvinyl pyrrolidone (hereinafter, sometimes referred to as "PVP") is preferred since it is relatively high in industrial availability. It is preferable to use two or more of hydrophilic polymers having different molecular weights. In this instance, the hydrophilic polymers preferably have different weight average molecular weights from one another by five times or more.

The spinning solution to be used for the preparation of the semipermeable membrane preferably comprises a hydrophobic polymer, a hydrophilic polymer, a solvent and an additive. The solvent may be an amphiprotic solvent which can fully dissolve all of the hydrophobic polymer, the hydrophilic polymer and the additive. Specific examples of the solvent include dimethylacetamide, dimethylformamide, dimethylsulfoxide, acetone, acetaldehyde and 2-methyl pyrrolidone. Dimethylacetamide is particularly preferred from the viewpoints of safety, stability and toxicity. The additive may be one which is a poor solvent for the hydrophobic polymer but is miscible with the hydrophilic polymer, such as an alcohol, glycerin, water and an ester. Water is particularly preferred from the viewpoint of process suitability.

The viscosity of the spinning solution for membrane production may depend on the molecular weight of the hydrophilic polymer, since commercially available hydrophilic polymers have low molecular weights. A decreased viscosity of the spinning solution could cause breakage or swinging of fibers during the preparation of a hollow fiber membrane, leading to a decreased stability of the resulting hollow fiber membrane. Accordingly, when PVP is used as the hydrophilic polymer, PVP with a high molecular weight is preferred. When two or more types of PVP are used in a mixture, the PVP mixture preferably has an average molecular weight of 200,000 or higher.

Next, the contents of the hydrophobic and hydrophilic polymers in the spinning solution is described. As stated above, as the polymer content increases, a membrane can be formed more effectively but the porosity of the resulting membrane decreases, leading to a decreased water permeability. Accordingly, there is an optimum range for the polymer content. To obtain a membrane that can exert both a high permselectivity and a low albumin permeability even when dried, like one produced in the present invention, the concentration of the hydrophobic polymer is preferably 10 to 20% by weight, more preferably 12 to 18% by weight, and the concentration of the hydrophilic polymer is preferably 2 to 20% by weight, more preferably 3 to 15% by weight. In the case where two or more hydrophilic polymers having different molecular weights are used, it is preferable that the content of hydrophilic polymers having molecular weights of 100,000 or higher in the spinning solution is 1 to 10% by weight. If this content is too large, the viscosity of the spinning solution increases, which may cause difficulty in formation of a membrane, as well as decrease in water permeability and diffusion performance. On the contrary, if this content is too small, it becomes impossible to construct a desirable network structure desired for the permeation of medium-to-high molecular weight uremia-toxic proteins.

When the hydrophobic polymer is a polysulfonic resin and the hydrophilic polymer is polyvinyl pyrrolidone, preferably the polyvinyl pyrrolidone in the semipermeable membrane is 1 to 10% by weight based on the content of the polysulfonic resin.

An embodiment of the process for preparing the semipermeable membrane is described hereinbelow. A spinning solution having a composition as mentioned above, along with a core solution, is extruded from a spinneret through an annular double slit tube to form a hollow fiber membrane. The membrane is washed with water, dried, and then crimped. The crimped membrane is taken up and cut to an appropriate length. The cut membranes are placed in a module case, in which both end faces of the bundle of the membranes are sealed with a potting material. In this manner, a hollow fiber membrane module is produced.

Preferably, the membrane is formed by a dry/wet spinning process, in which a dry zone is filled with dry mist. The dry mist refers to a mist-like material comprising water particles of 10 $\mu$m or smaller. The introduction of the dry mist into the dry zone can generate cores which may play an important role in the process for forming an outer surface of the hollow fiber membrane. PVP can coagulate around the cores to form PVP phases; thus, phase separation occurs in the dry zone. Subsequently, the fully grown PVP phases are removed in the coagulation bath, generating large pores. A conventional polysulfone dialyzing membrane generally has an asymmetric structure, where the permeation of material is controlled only through the inner surface. However, by providing such large pores on the outer surface of the membrane, an outer support layer having a coarse, porous structure can be formed. This structure enables a substance to be transferred through the membrane by diffusion more readily, thus providing an increased permeation performance to the finished dialyzing membrane.

In the present invention, for the formation of the hollow fiber membrane (not "module"), a conventional process including the treatment of the hollow fiber membrane with a moisture-retaining agent but not including any drying of the membrane is not employed and, instead, a process including the positive drying of the membrane is employed. As a result, a hollow fiber membrane of which water permeating performance after drying is ½ or higher relative to that before drying can be produced. Preferably, it should be 75% or higher, and more preferably it should be 90% or higher. In the process of the present invention, since the membrane is dried without the treatment with a moisture-retaining gent, the spinning solution should be designed taking the shrinking of the dried membrane in consideration. When the semipermeable membrane is used in this state particularly in an artificial kidney, however, a considerable amount of the hydrophilic polymer may diffuse from the membrane. For the purpose of reducing such elution, it is preferable that the membrane be subjected to a cross-linking treatment with gamma-ray irradiation, electron beam irradiation, or heat or chemical treatment. If gamma-ray is irradiated in the presence of air (i.e., oxygen), the breakage of the backbone of the hydrophilic polymer could occur by the action of excited oxygen radicals, resulting in the decomposition of the polymer. To solve this problem, it is preferable to saturate the membrane with water ratio of not smaller than 100% and not higher than 1000%, more preferably 100 to 600%, still more preferably 100 to 400% based on the dry weight of the membrane, replace the atmospheric air with an inert gas, and then irradiate the membrane with gamma-ray. Thus, elution of the hydrophilic polymer from the membrane can be prevented effectively. As the inert gas, nitrogen, argon, helium and carbon dioxide are preferably used. Nitrogen, which is inexpensive, is particularly preferred. The exposure dose of gamma-ray is preferably 10 to 50 KGy, more preferably 10 to 30 KGy. Since the cross-linking treatment induces the binding between the hydrophobic polymer and the hydrophilic polymer, elution of the hydrophilic polymer from the membrane can be reduced. The forced elution test of the membrane as described below demonstrated that any peak indicating the presence of the hydrophilic polymer eluted from the membrane was not observed. Accordingly, a semipermeable membrane having an elution amount of not higher than 10 ppm can be manufactured. The term "an elution amount" refers to the amount of the hydrophilic polymer in an extract that is prepared by dispersing or dissolving a certain amount of hollow fibers into a solvent which is a good solvent for both the hydrophobic and the hydrophilic polymers, has a solubility against the both polymers of not smaller than 0.5 g/ml and is immiscible with water, and then extracting the hydrophilic polymer from the solution with a certain amount of aqueous phase (0.1N ammonium chloride solution, pH 9.5) to give the extract. In the case where the hydrophilic polymer is a mixture of polysulfone and polyvinyl pyrrolidone, the good solvent is preferably methylene chloride.

The semipermeable membrane prepared as mentioned above characteristically exhibits good performance as a membrane for blood treatment, such as good diffusing capacity for uremia-causing substances and diffusion resistance against a useful protein albumin, and has a reduced elution of the hydrophilic polymer therefrom, due to the network structure formed with the hydrophobic and hydrophilic polymers. If the albumin permeability exceeds 3%, physical conditions of hypoalbuminemia patients or the nutritive conditions of elderly persons may affected. Therefore, the albumin permeability is preferably 3% or lower. The uremia-causing substance or uremic toxin may be urea, creatinine or uric acid. As the indicator of the substance permeation, vitamin B12 may be mentioned. In the semipermeable membrane of the present invention, the vitamin B12 clearance can be 135 ml/min or higher per 1.6 m². The clearance of urea, creatinine and uric acid is preferably 188, 175 and 165 ml/min, respectively, or higher per 1.6 m² in the practical viewpoint.

In order to achieve the above-stated properties, the content of the hydrophilic polymer in the membrane after the cross-linking should be 1 to 10%, and is preferably 2 to 6% by weight. Too small content may cause reduction in wetting ability against water and coagulation may occur upon contacting with blood. It is also preferable that the membrane after the cross-linking contain insoluble substances in a concentration of 5 to 15% by weight.

A stated above, the semipermeable membrane for blood treatment according to the present invention can exhibit a water permeability after drying of ½ or higher relative to that before drying, by employing a step of drying the membrane in the state where no moisture-retaining agent is attached to the membrane and a step of cross-linking the dried membrane after moisture conditioning (i.e., saturating with water). As a result, the membrane can be applied to a dialyzer which exhibits good properties such as decreased water permeability and less leaking of substances eluted from the membrane even when used after drying. The membrane of the present invention can be used in a dry or semi-dry state (as used herein, the term "semi-dry state" refers to a state where water is contained in the membrane but spaces between the hollow fibers are filled with a gas). Accordingly, a semipermeable membrane can be provided which is light-weight, almost free from the problem of freeze and easy to handle and has excellent performance. The production of such a semipermeable membrane may contribute to the reduced cost of the dialysis. Moreover, the membrane can exhibits a high dialyze performance at various temperatures and sterilization conditions since degradation in dialyze performance hardly occurs by drying. On the other hand, in the application to the treatment of a human body, elution of the hydrophilic polymer (a foreign substance to the body) can be reduced, leading to increased safety of the membrane as medical equipment. The dialyzer according to the present invention is applicable to medical apparatuses for blood treatment, such as an artificial kidney, a plasma separative membrane and a carrier for extracorporeal circulation adsorptive separation.

EXAMPLES

The invention will be described in more detail with reference to the working examples below. The determination methods employed are as follows.

(1) Determination of Water Permeability

A hydraulic pressure of 100 mmHg is applied to the inside of each hollow fiber in a glass tube mini-module (comprising 36 of hollow fibers; effective length—10 cm) in which both ends of the hollow fiber bundle are sealed), and then the amount of the permeate coming out of the mini-module per unit time period is measured.

The water permeation performance is calculated in accordance with the following equation:

$$UFR(\text{ml/hr/m}^2/\text{mmHg}) = \frac{Q_w}{P \times T \times A}$$

wherein $Q_w$ is the amount of the permeate (ml); $T$ is the efflux time (hr); $P$ is the pressure (mmHg); and $A$ is the area of the membrane (m²) (in terms of the are of the inner surface of the hollow fiber).

(2) Determination of Change in Performance Upon Drying

When no moisture-retaining agent is attached onto a hollow fiber to be tested, the fibers may be dried under the conditions below. However, when any moisture-retaining agent is attached, 10 g of the hollow fiber is soaked in 150 ml of pure water and allowed to stand for 24 hours. This procedure is repeated twice and then dried in the form of a fiber bundle at 100° C. for 24 hours. The water permeability is determined before and after the drying.

(3) Determination of Clearance of Solutes

This determination is performed in accordance with the description of "the Performance Evaluation Criteria for Dialyzers" (the Japanese Society of Artificial Organs, ed., issued on September, 1982). In this publication, there are shown two determination methods for clearance. In this example, the clearance is determined in accordance with the TMP 0 mmHg value. Among the solutes tested, vitamin B12 may be decomposed by irradiation with light. Accordingly, it is preferred to determine the clearance of vitamin B12 within the day of sampling, preferably immediately after the sampling. The clearance is determined using the equation below. When the areas of the membranes used for this test are different, the overall mass transfer coefficiency may be calculated based on the clearance value of each solute and the calculated value may be converted in area terms.

Clearance:

$$C_L(\text{ml/min}) = \frac{CBi - CBo}{CBi} \cdot Q_B$$

wherein $CB_i$ is the concentration at the module inlet; $CB_O$ is the concentration at the module outlet; and QB is the rate of liquid fed to the module (200 ml/min). QD (dialysate flow rate) is fixed to 500 ml/min.

(4) Determination of Albumin Permeability

Bovine blood (treated with heparin) with a hematocrit value of 30% and a total protein content of 6.5 g/dl, which has been kept at a temperature of 37° C.), in a blood tank is used. The bovine blood is fed to the inside of the hollow fibers through a pump at a rate of 200 ml/min. During this process, the pressure at the module outlet is adjusted to achieve a filtration rate of 20 ml/min per m² of the module area (which is equivalent to 32 ml/min per 1.6 m²), and the filtrate and the blood from the outlet are fed back to the blood tank. One hour after the start of reflux, the blood at the inlet and the outlet of the module and the filtrate are sampled. The blood samples are centrifuged to separate the serum. The serum is analyzed using the BCG (bromcresol green) method kit of A/G B-Test Wako (a tradename, Wako Pure Chemical Industries, Ltd.), and the albumin permeability (%) of the individual samples is calculated from the serum concentrations. For the determination of albumin concentration in the filtrate at high sensitivity, a calibration curve for albumin at low concentrations is established by making appropriate dilutions of serum albumin included in the kit.

$$\text{Albumin permeability (\%)} = \frac{2 \times C_F}{(CBi + CBo)} \times 100$$

wherein $C_F$, $CB_i$ and $CB_O$ are concentrations of albumin in the filtrate, at the module inlet and at the module outlet, respectively.

(5) Determination of concentration of a Hydrophilic Polymer PVP Transferred Into the Aqueous Layer in Forced Elution Test One liter of pure water is passed through the dialyzing module from the blood side to the dialyzate side to wash the module. 1 g of the hollow fiber from the module is dissolved in 10 ml of methylene chloride (10% w/v). The solution is extracted with 10 ml of 0.1N ammonium chloride solution (pH 9.5), and the resulting methylene chloride aqueous solution is supercentrifuted (20,000 rpm×15 min). The aqueous layer is passed through a filter (pore size: 0.5 μm) to obtain a sample solution.

Analysis of the sample solution is performed at 23° C. using two serially connected Toso TSK-gel-GMPWXL columns with a theoretical number of steps (8,900×2) under the following conditions: mobile phase—0.1N ammonium chloride solution (pH 9.5); flow rate—1.0 ml/min; sample loading—0.2 ml. Nine monodisperse polyethylene glycol products are used as the standard materials for calibration of molecular weight and a peak area-concentration calibration curve for a reference PVP product is established. The concentration of PVP transferred into the aqueous layer (5 ml) is determined from the PVP peak area of each sample solution. Samples containing a detectable amount of PVP are determined on the recovery of PVP (i.e., transfer rate into the aqueous layer) from that of the reference, and the amount of PVP eluted into the aqueous layer is calculated from the PVP concentration in the aqueous layer based on the recovery.

(6) Determination of PVP Content by Elemental Analysis

A sample irradiated with gamma-ray is dried at ordinary temperature using a vacuum pump. 10 mg of the dried sample is analyzed using a CHN elemental analyzer. The PVP content is calculated from the nitrogen content.

(7) Determination of Insoluble Material Content 10 g of a hollow fiber irradiated with gamma-ray is dissolved in 100 ml of dimethylformamide. The solution is centrifuged at 1,500 rpm for 10 min to separate insoluble materials, and the supernatant is discarded. This procedure is repeated three times. The insoluble material is washed with 100 ml of pure water, and then centrifuged three times as mentioned above. The resulting solid material is evaporated to dryness and then dried with a vacuum pump. The weight of the dried solid material is used to calculate the content of the insoluble materials.

Example 1

Four parts of polysulfone (Amoco, Udel-P3500), 12 parts of polysulfone (Amoco, Udel-P1700), 4 parts of polyvinyl pyrrolidone (International Special Products, hereinafter, referred to as "ISP"; K30) and 2 parts of polyvinyl pyrrolidone (ISP, K90) were dissolved in 77 parts of dimethylacetamide and 1 part of water with heating, to obtain a spinning solution for membrane formation.

The viscosity of the spinning solution was 13.4 Pa·s at 50° C. The spinning solution was introduced to a spinneret at 50° C., and extruded, along with a core solution comprising 65 parts of dimethylacetamide and 35 parts of water, from the spinneret through an annular double slit tube having an outside diameter of 0.35 mm and an inside diameter of 0.25 mm, whereby a hollow fiber membrane was formed. The membrane was subjected to moisture conditioning at 30° C. and a dew point of 28° C. The conditioned membrane was passed through a dry zone atmosphere which had a length of 250 mm and contained dry mist of 10 μm or smaller, then through a coagulation bath at 40° C., comprising 20 wt % of dimethylacetamide and 80 wt % of water. The resulting membrane was subjected to a washing step with water at 80° C. for 60 sec, a drying process at 135° C. for 2 min, and then a crimping step at 160° C. The resulting membrane was taken up into a bundle. The hollow fiber membrane bundle was packaged in a module case so that the area of the hollow fiber membrane became 1.6 m$^2$, and potted. The potted bundle was provided with opening faces at the both ends to form a dialyzing module. Thereafter, blood side was filled with deaerated warmed water (37° C.) at a feed rate of 200 ml/min for 1 min and, then, an inert gas (nitrogen) was fed to the module at a pressure of 0.1 MPa for 15 sec to force out the filling water therefrom. In this state, the water content in the hollow fiber membrane was 320%.

The dialyzate side was also replaced with the inert gas. The module was irradiated with gamma-ray (25 KGy) in the state where the membrane was wet and the inert gas was filled therein. Determination of water permeation performance, clearance of each solute and albumin permeability was performed. As a result, it was demonstrated that the module had the clearance of urea, creatinine, uric acid, phosphoric acid and VB12 of 195 ml/min, 185 ml/min, 180 ml/min, 186 ml/min and 145 ml/min, respectively, and the water permeation performance of 756 ml/hr/m$^2$/mmHg, and the albumin permeability of 1.5%.

After dried, the water content in the membrane was 0%, the water permeation performance of the hollow fiber was 772 ml/hr/m$^2$/mmHg, and no degradation in performance was observed. The PVP content in the hollow fiber membrane was determined by elemental analysis and found to be 3.5%. The insoluble material content in the hollow fiber after irradiation with gamma-ray was determined and found to be 7.2%. When the forced elution test was performed to determine the concentration of PVP transferred from the hollow fiber membrane into the aqueous layer, no peak was detected and therefore PVP was not detected.

Example 2

Four parts of polysulfone (Amoco, Udel-P3500), 12 parts of polysulfone (Amoco, Udel-P1700), 3 parts of polyvinyl pyrrolidone (ISP, K30) and 3 parts of polyvinyl pyrrolidone (ISP, K90) were dissolved in 77 parts of dimethylacetamide and 1 part of water with heating, to obtain a spinning solution for membrane formation. The viscosity of the spinning solution was 18 Pa·s at 50° C. A module was fabricated in the same manner as in Example 1. The water content in the hollow fiber membrane after forcing out water from the membrane was 330%. The dialyzate side was also replaced with the inert gas. The module was irradiated with gamma-ray (25 KGy) in the state where the membrane was wet and the inert gas was filled therein. Determination of water permeation performance, clearance of each solute and albumin permeability was performed. As a result, it was shown that the module had the clearance of urea, creatinine, uric acid, phosphoric acid and VB12 of 193 ml/min, 182 ml/min, 178 ml/min, 184 ml/min and 142 ml/min, respectively, and the water permeation performance of 720 ml/hr/m$^2$/mmHg, and the albumin permeability of 1.8%. After dried, the water content in the membrane was 0%, the water permeation performance of the hollow fiber was 734 ml/hr/m$^2$/mmHg, and no degradation in performance was observed.

The PVP content in the hollow fiber membrane was determined by elemental analysis and found to be 4.0%. The insoluble material content in the hollow fiber after irradiation with gamma-ray was determined and found to be 7.8%. When the forced elution test was performed to determine the concentration of PVP transferred from the hollow fiber membrane into the aqueous layer, PVP was not detected, as in the case of Example 1.

Example 3

Four parts of polysulfone (Amoco, Udel-P3500), 12 parts of polysulfone (Amoco, Udel-P1700), 2 parts of polyvinyl pyrrolidone (ISP, K30) and 4 parts of polyvinyl pyrrolidone (ISP, K90) were dissolved in 77 parts of dimethylacetamide and 1 part of water with heating, to obtain a spinning solution for membrane formation. The viscosity of the spinning solution was 23 Pa·s at 50° C. A module was fabricated in the same manner as in Example 1.

The water content in the hollow fiber membrane after forcing out water from the membrane was 400%. The dialyzate side was also replaced with the inert gas. The module was irradiated with gamma-ray (25 KGy) in the state where the membrane was wet and the inert gas was filled therein. Determination of water permeation performance, clearance of each solute and albumin permeability was performed. As a result, it was shown that the module had the water permeation performance of 702 ml/hr/m$^2$/mmHg, the clearance of urea, creatinine, uric acid, phosphoric acid and VB12 of 191 ml/min, 180 ml/min, 175 ml/min, 181 ml/min and 140 ml/min, respectively, and the albumin permeability of 1.0%. After dried, the water content in the membrane was 0%, the water permeation performance of the hollow fiber was 727 ml/hr/m$^2$/mmHg, and no degradation in performance was observed.

The PVP content in the hollow fiber membrane was determined by elemental analysis and found to be 4.7%. The insoluble material content in the hollow fiber after irradiation with gamma-ray was determined and found to be 8.3%. When the forced elution test was performed to determine the concentration of PVP transferred from the hollow fiber membrane into the aqueous layer, PVP was not detected, as in the case of Example 1.

Example 4

Four parts of polysulfone (Amoco, Udel-P3500), 12 parts of polysulfone (Amoco, Udel-P1700), 1 part of polyvinyl pyrrolidone (ISP, K30) and 5 parts of polyvinyl pyrrolidone (ISP, K90) were dissolved in 77 parts of dimethylacetamide and 1 part of water with heating, to obtain a spinning solution for membrane formation. The viscosity of the spinning solution was 29 Pa·s at 50° C. A module was fabricated in the same manner as in Example 1.

The water content in the hollow fiber membrane after forcing out water from the membrane was 380%. The dialyzate side was also replaced with the inert gas. The module was irradiated with gamma-ray (25 KGy) in the state where the membrane was wet and the inert gas was filled therein. Determination of water permeation performance, clearance of each solute and albumin permeability was performed. As a result, it was shown that the module had the water permeation performance of 675 ml/hr/m$^2$/mmHg, the clearance of urea, creatinine, uric acid, phosphoric acid and VB12 of 190 ml/min, 179 ml/min, 173 ml/min, 179 ml/min and 138 ml/min, respectively, and the albumin permeability of 0.9%. After dried, the water content in the membrane was 0%, the water permeation performance of the hollow fiber was 668 ml/hr/m$^2$/mmHg, and no degradation in performance was observed.

The PVP content in the hollow fiber membrane was determined by elemental analysis and found to be 5.1%. The insoluble material content in the hollow fiber after irradiation with gamma-ray was determined and found to be 8.9%. When the forced elution test was performed to determine the concentration of PVP transferred from the hollow fiber membrane into the aqueous layer, PVP was not detected, as in the case of Example 1.

Example 5

Four parts of polysulfone (Amoco, Udel-P3500), 12 parts of polysulfone (Amoco, Udel-P1700) and 6 parts of polyvinyl pyrrolidone (ISP, K90) were dissolved in 77 parts of dimethylacetamide and 1 part of water with heating, to obtain a spinning solution for membrane formation. The viscosity of the spinning solution was 38 Pa·s at 50° C. A module was fabricated in the same manner as in Example 1.

The water content in the hollow fiber membrane after forcing out water from the membrane was 350%. The dialyzate side was also replaced with the inert gas. The module was irradiated with gamma-ray (25 KGy) in the state where the membrane was wet and the inert gas was filled therein. Determination of water permeation performance, clearance of each solute and albumin permeability was performed. As a result, it was shown that the module had the water permeation performance of 620 ml/hr/m$^2$/mmHg, the clearance of urea, creatinine, uric acid, phosphoric acid and VB12 of 189 ml/min, 177 ml/min, 169 ml/min, 178 ml/min and 137 ml/min, respectively, and the albumin permeability of 0.8%. After dried, the water content in the membrane was 0%, the water permeation performance of the hollow fiber was 656 ml/hr/m$^2$/mmHg, and no degradation in performance was observed.

The PVP content in the hollow fiber membrane was determined by elemental analysis and found to be 5.5%. The insoluble material content in the hollow fiber after irradiation with gamma-ray was determined and found to be 9.2%. When the forced elution test was performed to determine the concentration of PVP transferred from the hollow fiber membrane into the aqueous layer, PVP was not detected, as in the case of Example 1.

Example 6

Sixteen parts of polysulfone (Amoco, Udel-P3500), 4 parts of polyvinyl pyrrolidone (ISP, K30), and 2 parts of polyvinyl pyrrolidone (ISP, K90) were dissolved in 77 parts of dimethylacetamide and 1 part of water with heating, to obtain a spinning solution for membrane formation. The viscosity of the spinning solution was 14.0 Pa·s at 50° C. A module was fabricated in the same manner as in Example 1.

The water content in the hollow fiber membrane after forcing out water from the membrane was 260%. The dialyzate side was also replaced with the inert gas. The module was irradiated with gamma-ray (25 KGy) in the state where the membrane was wet and the inert gas was filled therein. Determination of water permeation performance, clearance of each solute and albumin permeability was performed. As a result, it was shown that the module had the water permeation performance of 330 ml/hr/m$^2$/mmHg, the clearance of urea, creatinine, uric acid, phosphoric acid and VB12 of 195 ml/min, 185 ml/min, 180 ml/min, 187 ml/min and 145 ml/min, respectively, and the albumin permeability of 0.5%. After dried, the water content in the membrane was 0%, the water permeation performance of the hollow fiber was 360 ml/hr/m2/mmllg, and no degradation in performance was observed.

The PVP content in the hollow fiber membrane was determined by elemental analysis and found to be 3.1%. The insoluble material content in the hollow fiber after irradiation with gamma-ray was determined and found to be 7.5%. When the forced elution test was performed to determine the concentration of PVP transferred from the hollow fiber membrane into the aqueous layer, PVP was not detected, as in the case of Example 1.

Comparative Example 1

Eighteen parts of polysulfone (Amoco, Udel-P3500), 6 parts of polyvinyl pyrrolidone (BASF, K30) and 3 parts of polyvinyl pyrrolidone (BASF, K90) were dissolved in 72 parts of dimethylacetamide and 1 part of water with heating, to obtain a spinning solution for membrane formation. The viscosity of the spinning solution was 70 Pa·s at 30° C. The spinning solution was introduced to a spinneret at 50° C., and extruded, along with a core solution comprising 65 parts of dimethylacetamide and 35 parts of water, from the spinneret through an annular double slit tube having an outside diameter of 0.35 mm and an inside diameter of 0.25 mm, whereby a hollow fiber membrane was formed. The membrane was subjected to moisture conditioning at 30° C. and a dew point of 28° C. The conditioned membrane was passed through a dry zone which had a length of 250 mm, then through a coagulation bath at 40° C. comprising 20 wt % of dimethylacetamide and 80 wt % of water. The resulting membrane was subjected to a washing step with water at 80° C. for 20 sec, and then a moisture conditioning step with a glycerin solution. After taking off the glycerin solution, the resulting membrane was packaged in a module case, and then potted. The potted bundle was provided with opening faces at the both ends to form a dialyzing module. Thereafter, the module was washed to remove free glycerin therefrom, filled with water, and then irradiated with gamma-ray (25 KGy). Determination of water permeation performance, clearance of each solute and albumin permeability was performed. As a result, it was demonstrated that the module had the clearance of urea, creatinine, uric acid, phosphoric acid and VB12 of 194 ml/min, 185 ml/min, 176 ml/min, 183 ml/min and 135 ml/min, respectively, and the water permeation performance of 716 ml/hr/m$^2$/mmHg, and the albumin permeability of 0.7%.

The PVP content in the hollow fiber membrane was determined by elemental analysis and found to be 4.5%. The insoluble material content in the hollow fiber after irradiation with gamma-ray was determined and found to be 8.0%. When the forced elution test was performed to determine the concentration of PVP transferred from the hollow fiber membrane into the aqueous layer, PVP was not detected, as in the case of Example 1. Next, the liquid filled in the module was removed. After drying the membrane with a drier, the determination of the water permeation performance, clearance of each solute and albumin permeability was performed again. As a result, it was demonstrated that the module had the clearance of urea, creatinine, uric acid, phosphoric acid and VB12 of 186 ml/min, 177 ml/min, 169 ml/min, 176 ml/min and 119 ml/min, respectively, the water permeability of 0%, the water permeation performance of 10 ml/hr/m$^2$/mmHg, and the albumin permeability of 0.1%. Thus, the membrane showed remarkable degradation in performance after drying. When a portion of the hollow fiber before drying was taken out of the module and dried in the same manner as described above, similar degradation in performance was also observed.

Comparative Example 2

Seventeen parts of polysulfone (Amoco, Udel-P3500), 5 parts of polyvinyl pyrrolidone (BASF, K30) and 4 parts of polyvinyl pyrrolidone (BASF, K90) were dissolved in 73 parts of dimethylacetamide and 1 part of water with heating, to obtain a spinning solution for membrane formation. The viscosity of the spinning solution was 40 Pa·s at 50° C. A module was fabricated in the same manner as in Comparative Example 1. The module was irradiated with gamma-ray in the state where water is filled in the module. Determination of water permeation performance, clearance of each solute and albumin permeability of the module was performed. As a result, it was demonstrated that the module had the clearance of urea, creatinine, uric acid, phosphoric acid and VB12 of 195 ml/min, 186 ml/min, 177 ml/min, 184 ml/min and 137 ml/min, respectively, and the water permeation performance of 600 ml/hr/m$^2$/mmHg, and the albumin permeability of 1.2%.

The PVP content in the hollow fiber membrane was determined by elemental analysis and found to be 4.8%. The insoluble material content in the hollow fiber was determined and found to be 10.0%. When the forced elution test was performed to determine the concentration of PVP transferred from the hollow fiber membrane into the aqueous layer, PVP was not detected, as in the case of Example 1. Next, the liquid filled in the module was removed. After drying the membrane with a drier, the determination of the water permeation performance, clearance of each solute and albumin permeability was performed again. As a result, it was demonstrated that the module had the clearance of urea, creatinine, uric acid, phosphoric acid and VB12 of 189 ml/min, 179 ml/min, 172 ml/min, 178 ml/min and 126 ml/min, respectively, the water permeability of 0%, the water permeation performance of 200 ml/hr/m$^2$/mmHg, and the albumin permeability of 0.2%. Thus, the membrane showed remarkable degradation in performance after drying. When a portion of the hollow fiber before drying was taken out of the module and dried in the same manner as described above, similar degradation in performance was also observed.

Comparative Example 3

Seventeen parts of polysulfone (Amoco, Udel-P3500), 5 parts of polyvinyl pyrrolidone (BASF, K30) and 3 parts of polyvinyl pyrrolidone (BASF, K90) were dissolved in 74 parts of dimethylacetamide and 1 part of water with heating, to obtain a spinning solution for membrane formation. The viscosity of the spinning solution was 33 Pa·s at 50° C. A module was fabricated in the same manner as in Comparative Example 1. The module was irradiated with gamma-ray in the state where water is filled in the module. Determination of water permeation performance, clearance of each solute and albumin permeability was performed. As a result, it was demonstrated that the module had the clearance of urea, creatinine, uric acid, phosphoric acid and VB12 of 196 ml/min, 187 ml/min, 178 ml/min, 185 ml/min and 138 ml/min, respectively, and the water permeation performance of 525 ml/hr/m$^2$/mmHg, and the albumin permeability of 0.8%.

The PVP content in the hollow fiber membrane was determined by elemental analysis and found to be 4.0%. The insoluble material content in the hollow fiber was determined and found to be 9.3%. When the forced elution test was performed to determine the concentration of PVP transferred from the hollow fiber membrane into the aqueous layer, PVP was not detected, as in the case of Example 1. Next, the liquid filled in the module was removed. After drying the membrane with a drier, the determination of the water permeation performance, clearance of each solute and albumin permeability was performed again. As a result, it was demonstrated that the module had the clearance of urea, creatinine, uric acid, phosphoric acid and VB12 of 191 ml/min, 181 ml/min, 173 ml/min, 180 ml/min and 126 ml/min, respectively, the water permeability of 0%, the water permeation performance of 340 ml/hr/m$^2$/mmHg, and the albumin permeability of 0.5%. Thus, the membrane showed remarkable degradation in performance after drying. When a portion of the hollow fiber before drying was taken out of the module and dried in the same manner as described above, similar degradation in performance was also observed.

Comparative Example 4

Sixteen parts of polysulfone (Amoco, Udel-P3500), 4 parts of polyvinyl pyrrolidone (ISP, K30) and 2 parts of polyvinyl pyrrolidone (ISP, K90) were dissolved in 77 parts of dimethylacetamide and 1 part of water with heating, to obtain a spinning solution for membrane formation. The viscosity of the spinning solution was 14.0 Pa·s at 50° C. A module was fabricated in the same manner as in Example 1, except that the dry zone was not dry mist atmosphere.

The water content in the hollow fiber membrane after forcing out water from the membrane was 230%. The dialyzate side was also replaced with the inert gas. The membrane was irradiated with gamma-ray (25 KGy) in the state where the membrane was wet and the inert gas was filled therein. Determination of water permeation performance, clearance of each solute and albumin permeability was performed. As a result, it was shown that the module had the water permeation performance of 350 ml/hr/m2/mmHg, the clearance of urea, creatinine, uric acid, phosphoric acid and VB12 of 190 ml/min, 180 ml/min, 175 ml/min, 182 ml/min and 138 ml/min, respectively, and the albumin permeability of 0.6%. After dried, the water content in the membrane was 0%, the water permeation performance of the hollow fiber was 340 ml/hr/m$^2$/mmHg, and no degradation in performance was observed.

The PVP content in the hollow fiber membrane was determined by elemental analysis and found to be 3.3%. The insoluble material content in the hollow fiber after irradiation with gamma-ray was determined and found to be 7.8%. When the forced elution test was performed to determine the concentration of PVP transferred from the hollow fiber membrane into the aqueous layer, PVP was not detected, as in the case of Example 1.

Comparative Example 5

Sixteen parts of polysulfone (Amoco, Udel-P3500), 4 parts of polyvinyl pyrrolidone (ISP, K30) and 2 parts of polyvinyl pyrrolidone (ISP, K90) were dissolved in 77 parts of dimethylacetamide and 1 part of water with heating, to obtain a spinning solution for membrane formation. The viscosity of the spinning solution was 14.0 Pa·s at 50° C. A module was fabricated in the same manner as in Example 1, except that the water filled in the membrane was forced out with compressed air and the atmosphere was not replaced with any inert gas. The water content in the hollow fiber membrane in this state was 260%. The membrane was irradiated with gamma-ray (25 KGy) in the state where air was filled therein and the membrane was wet. Determination of water permeation performance, clearance of each solute and albumin permeability was performed. As a result, it was shown that the module had the water permeation performance of 350 ml/hr/m$^2$/mmHg, the clearance of urea, creatinine, uric acid, phosphoric acid and VB12 of 195 ml/min, 185 ml/min, 180 ml/min, 187 ml/min and 145 ml/min, respectively, and the albumin permeability of 0.5%. After dried, the water content in the membrane was 0%, the water permeation performance of the hollow fiber was 340 ml/hr/m$^2$/mmHg, and no degradation in performance was observed.

The PVP content in the hollow fiber membrane was determined by elemental analysis and found to be 3.1%. The insoluble material content in the hollow fiber after irradiation with gamma-ray was determined and found to be 7.8%. When the forced elution test was performed to determine the concentration of PVP transferred from the hollow fiber membrane into the aqueous layer, however, 1255 ppm of PVP was detected in the aqueous layer.

According to the present invention, a dialyzer for blood treatment which has incorporated therein a dry-type semipermeable membrane having advantages such as light-weight and free from the problem of freeze, wherein the semipermeable membrane has good water permeability and dialyze performance; a dialyzer for blood treatment which is light-weight, easy to handle, and exhibits a reduced elution of a hydrophilic polymer; and a process for producing a semipermeable membrane for blood treatment suitable for the dialyzers.

TABLE 1

|  | Examples | | | | | | Comparative Examples | | | | |
| --- | --- | --- | --- | --- | --- | --- | --- | --- | --- | --- | --- |
|  | 1 | 2 | 3 | 4 | 5 | 6 | 1 | 2 | 3 | 4 | 5 |
| Water permeation performance after-dry/before-dry | 772/756 | 734/720 | 727/702 | 668/675 | 656/620 | 360/330 | 10/716 | 200/600 ca. 1/3 | 340/525 ca. 2/3 | 350/340 | 350/340 |
| PSF/PVP (K30/K90) | 16(4/2) | 16(3/3) | 15(2/4) | 16(1/5) | 16(0/6) | 16(4/2) | 18(6/3) | 17(5/4) | 17(5/3) | 16(4/2) | 16(4/2) |
| Dry zone | Dry mist | | | | | | No mist | | | | Dry mist |
| Filled gas | | | | | $N_2$ | | | | | | Air |
| Liquid content at γ-ray irradiation (%) | 320 | 330 | 400 | 380 | 350 | 260 | >1000 | >1000 | >1000 | 230 | 260 |
| PVP content (%) | 3.5 | 4.0 | 4.7 | 5.1 | 5.5 | 3.1 | 4.5 | 4.8 | 4.0 | 3.3 | 3.1 |
| Albumin permeability (%) | 1.5 | 1.8 | 1.0 | 0.9 | 0.8 | 0.5 | 0.1 | 0.2 | 0.5 | 0.6 | 0.5 |
| Urea (pre/post) ml/min | 195 | 193 | 191 | 190 | 189 | 195 | 194/188 | 195/189 | 196/191 | 190 | 195 |
| Cr (pre/post) | 185 | 182 | 180 | 179 | 177 | 185 | 185/177 | 186/179 | 187/181 | 180 | 185 |
| Ureic acid (pre/post) | 180 | 178 | 175 | 173 | 169 | 180 | 176/169 | 177/172 | 178/173 | 175 | 180 |
| Phosphoric acid (pre/post) | 186 | 184 | 181 | 179 | 178 | 187 | 183/176 | 184/178 | 185/180 | 182 | 187 |
| Vitamin (pre/post) | 145 | 142 | 140 | 138 | 137 | 145 | 135/119 | 137/126 | 138/126 | 138 | 145 |
| PVP elution (PPM) | 0 | 0 | 0 | 0 | 0 | 0 | 0 | 0 | 0 | 0 | 1255 |
| Insoluble substances (%) | 7.2 | 7.8 | 8.3 | 8.9 | 9.2 | 7.5 | 8.0 | 10.0 | 9.3 | 7.8 | 7.8 |

What is claimed is:

1. A dialyzer for blood treatment having incorporated therein a dry or semi-dry semipermeable membrane having a water permeation of 330 ml/hr/m$^2$/mmHg or more before drying which comprises a polysulfonic resin and polyvinyl pyrrolidone in an amount of 1 to 10% by weight based on the content of the polysulfonic resin, the water permeating performance of the semipermeable membrane after drying being ½ or higher relative to that before drying, the dialyzer satisfying any of the following requirements:

(A) the vitamin B12 clearance is not smaller than 135 ml/min per 1.6 m$^2$; and (B) the amount of the hydrophilic polymer that is eluted from the semipermeable membrane is not higher than 10 ppm.

2. The dialyzer according to claim 1, wherein the water permeating performance of the semipermeable membrane after drying being 75% or higher relative to that before drying.

3. The dialyzer according to claim 1, wherein the water permeating performance of the semipermeable membrane after drying being 90% or higher relative to that before drying.

4. The dialyzer according to claim 1, wherein the albumin permeability is not higher than 30%.

* * * * *